(12) United States Patent
Hsieh

(10) Patent No.: US 6,894,029 B1
(45) Date of Patent: May 17, 2005

(54) USE OF JELLYFISH COLLAGEN (TYPE II) IN THE TREATMENT OF RHEUMATOID ARTHRITIS

(75) Inventor: Yun-Hwa Peggy Hsieh, Auburn, AL (US)

(73) Assignee: Auburn University, Auburn, AL (US)

( * ) Notice: Subject to any disclaimer, the term of this patent is extended or adjusted under 35 U.S.C. 154(b) by 351 days.

(21) Appl. No.: 10/007,716

(22) Filed: Nov. 13, 2001

Related U.S. Application Data
(60) Provisional application No. 60/248,318, filed on Nov. 13, 2000.

(51) Int. Cl.[7] .................. A61K 38/00; A61K 38/17; A23J 1/00
(52) U.S. Cl. ................. 514/21; 514/2; 514/825; 514/885; 530/356; 530/418; 530/422; 530/427; 424/184.1
(58) Field of Search .............. 514/21, 2, 825; 514/885; 530/356, 418, 422, 427; 424/184.1

(56) References Cited

U.S. PATENT DOCUMENTS

| | | | |
|---|---|---|---|
| 5,399,347 A | 3/1995 | Trentham et al. | 424/184.1 |
| 5,714,582 A | * 2/1998 | Wolfinbarger | 530/356 |
| 5,843,445 A | * 12/1998 | Weiner et al. | 424/184.1 |
| 5,925,736 A | * 7/1999 | Neff et al. | 530/356 |

OTHER PUBLICATIONS

Trentham et al., "Effects of Oral Administration of Type II Collagen on Rheumatoid Arthritis," *Science*, Sep. 24, 1993, pp. 1727–1730, vol. 261, Issue 5129.

* cited by examiner

*Primary Examiner*—Jon Weber
*Assistant Examiner*—Abdel A. Mohamed
(74) *Attorney, Agent, or Firm*—Alston & Bird LLP

(57) ABSTRACT

Compositions of substantially homogeneous type II-like collagen from invertebrates belonging to the class Scyphozoa, phylum Coelenterata, i.e., jellyfish, particularly *Stomolophus meleagris*, and methods for its extraction are provided. Methods for the treatment of arthritis, in particular rheumatoid arthritis, by administering an effective amount of the collagen-containing compositions of the invention so as to induce immune tolerance, are also provided.

15 Claims, 5 Drawing Sheets

USE OF JELLYFISH COLLAGEN (TYPE II) IN THE TREATMENT OF RHEUMATOID ARTHRITIS

CROSS-REFERENCE TO RELATED APPLICATIONS

This application claims the benefit of U.S. Provisional Application No. 60/248,318, filed Nov. 13, 2000, which is hereby incorporated in its entirety by reference herein.

FIELD OF THE INVENTION

The invention relates to collagen compositions, methods for extracting such compositions from jellyfish, and formulations and methods useful in the treatment of arthritis.

BACKGROUND OF THE INVENTION

An edible species known as cannonball jellyfish (*Stomolophus meleagris*) is abundant in coastal waters from North Carolina to Florida and in the northern Gulf of Mexico. Cannonballs surface each fall in drifts of millions. They drag down shrimpers' nets, litter beaches, sting swimmers, eat valuable oyster and clam larvae, and clog the intake valves of power plants (Moller (1980) *Meeresforchung* 28:90–100; Rudloe (1988) *The Wilderness Coast* (E. P. Dutton, N.Y.)). Cannonball jellyfish have an abundance of proteins and minerals. Analysis of the amino acid composition of mesogloea hydrolysate shows that glycine is the most abundant amino acid, and that hydroxyproline and hydroxylysine, which are characteristic of collagen, are present. Jellyfish proteins, made almost entirely of collagen (roughly 80 to 90%), are rich in hydroxylysine and its glycosides. Kimura et al. (1983) *J. Food Sci.* 48:1758–1569.

Based on a study of *Stomolophus nomurai*, Kimura et al. reported that the major carbohydrate moiety in jellyfish collagen was the disaccharide unit glucosylgalactose. These results confirmed similar earlier findings reported by Rigby et al. (1972) *Aus. J. Biol. Sci.* 25:1361–3. The SDS-PAGE electrophoretic pattern revealed that the mesogloea collagen was composed of two electrophoretically distinct protein chains. Kimura et al. In contrast to jellyfish skin collagen, the mesogloea collagen was found to lack disulfide linkages based on unchanged electrophoretic mobility after treatment with the reducing agent, dithiothreitol.

In 1985, Miura et al. (1985) *J. Biol. Chem.* 260:15352–6, suggested that the primary mesogloea collagen of the jellyfish *Stomolophus nomurai* was type V, a heterotrimer of $\alpha 1$, $\alpha 2$, and $\alpha 3$ chains. On the other hand, Nagai et al. (1999) *J. Sci. Food Agric.* 79:855–858, reported that the collagen isolated from *Stomolophus meleagris* was type I, composed of $\alpha 1 \alpha 2 \alpha 3$-heterotrimers. The authors attributed the third chain to an exceptional type I chain present in the skin of many teleosts. Nagai et al. later reported a fourth subunit ($\alpha 4$) in *Rhopilema asamushi* jellyfish. Nagai et al. (2000) *Food Chem.* 70:205–208.

Collagen is generally unique to the organism, or even the type of tissue, from which it is derived. A detailed description of the structure and the biological functions of the various different types of naturally occurring collagens can be found in Lodish, ed. (1999) *Molecular Cell Biology*, 4th ed., (W H Freeman & Co, N.Y.). Type II collagen from chicken and cows has been used to treat rheumatoid arthritis (RA), an autoimmune disease characterized by pain, warmth, redness, swelling, and stiffness of the joints, often resulting in progressive joint destruction, deformity, and loss of function. Specifically, type II collagen has been used to induce oral tolerance in a subject suffering from RA.

Oral tolerance, first described in 1911 by Wells, refers to a state of specific immunological hyporesponsiveness to orally administered antigen. It is a long recognized method of inducing immune tolerance. The primary mechanisms by which oral tolerance is mediated include deletion, anergy, and active cellular suppression. Weiner et al. (1997) *Res. Immunol.* 148:528–33. The dose of the orally administered antigen determines mode, i.e., low doses favor active suppression, whereas high doses favor deletion and anergy. Friedman et al. (1994) *Chem. Immunol.* 58:259–90. Other parameters, such as feeding repetitions, forms of antigen, timing of administration, etc., can also influence effectiveness of oral tolerance. Oral tolerance involves the activation of suppressor T cells in the mucosa of the gut. Weiner et al. (1994) *Annu. Rev. Immunol.* 12:809–37.

Orally administered autoantigens suppressed autoimmunity in several animal disease models, including experimental autoimmune encephalomyelitis, Miller et al. (1993) *J. NeuroimmunoL* 46:73–82, uveitis, Nussenblatt et al. (1990) *J. Immunol.* 144(5):1689–95, myasthenia, Wang et al. (1993) *J. NeuroimmunoL* 44:209–14, diabetes (non-obese mouse model), Daniel et al. (1996) *Proc. Natl. Acad. Sci.* 93:956–60, and in adjuvant induced arthritis and collagen induced arthritis, Khare et al. (1995) *J. Immunol.* 155:3653–9; Matsumoto et al. (1998) *Clin. Immunol, Immunopathol.* 88:70–9; Yoshino et al. (1997) *Arthrit. Rheumat.* 38:1092–96.

Human clinical trials involving oral tolerance have been carried out for diseases such as multiple sclerosis, Weiner et al. (1994), food intolerance, Ferguson et al. (1996) *Ann. N.Y. Acad. Sci.* 778:202–16, and uveitis, Nussenblatt et al. (1996) *Ann. N.Y. Acad. Sci.* 778:325–37. Decreases in T-cell autoreactivity and other positive clinical effects have been observed, with relatively few or no negative side-effects.

Chicken and bovine type II collagen has been tested as a candidate autoantigen for inducing oral tolerance (a tolerizing antigen) in several animal models, including antigen-induced arthritis, Yoshino et al. (1995) *Arthritis Rheum.* 38:1092–6, adjuvant arthritis, Zhang et al. (1990) *J. Immunol.* 145:2489–93, pristane-induced arthritis, Thompson et al. (1993) *Immunology* 79:152–7, and collagen-induced arthritis, Thompson et al. (1986) *Clin. Exp. Immunol.* 64:581–6. Collagen-induced arthritis (CLA), for example, shares clinical, histological, immunological, and genetic features with human RA and has been used as an animal model for the study of RA for over twenty years.

Chicken and bovine type II collagen has also been found to confer a suppressing effect on RA in humans. For instance, oral administration of a solution of type II collagen prepared from chicken cartilage was successfully used to treat a group of 60 patients with severe RA by inducing oral tolerance. See Baringa et al. (1993) *Science* 261:1669–70 and Trentham et al. (1993) *Science* 261(5129):1727–30. Researchers at the Harvard Medical School have reported that in a randomized, double-blind trial, a decrease in the number of swollen joints and tender joints occurred in subjects fed chicken type II collagen for 3 months but not in those that received a placebo; four patients in the collagen group had complete remission of the disease. The researchers concluded that oral tolerance had therapeutic efficacy for rheumatoid arthritis.

World-wide, 1% of the human population is afflicted with RA. In the United States, roughly 2% of the American population suffers from RA. For example, a 1990 study found that roughly 2.1 million American with RA, mostly persons between 20 and 45 years of age, with a higher frequency in females. Singsen (1990) *Rheum. Dis. Clin. North. Am.* 16:581–99. Thus, type II collagen, or collagen having similar effects, has great potential for the relief of RA in a significant number of people. Current treatment options are often unsatisfactory because of both limited efficacy and negative side-effects, such as toxicity.

Thus, due to its relative lack of side-effects, oral tolerance offers significant potential for the relief of RA. Sources of type II collagen that have been used in RA oral tolerance studies include native type II collagen from nonlathyritic chicken sternal cartilage, Trentham et al., and type II collagen from the nasal septum of cows, Sieper et al. (1996) *Arthritis Rheum.* 39:41–51. However, such sources are relatively expensive to obtain. Further, negative effects from delayed type hypersensitivity (DTH) have been noted, for instance, with bovine type II collagen. Of additional concern is the presence of bovine spongiform encepalopathy (BSE) in cattle and the possibility of transmission to humans fed bovine type II collagen. Accordingly, cost-effective sources of high-quality, safe, efficacious type II collagen, or collagen able to induce oral tolerance, are needed.

SUMMARY OF THE INVENTION

The subject invention provides novel compositions of substantially homogeneous type II-like collagen from invertebrates belonging to the class Scyphozoa, phylum Coelenterata, more particularly jellyfish. The invention includes a composition comprising substantially homogeneous type II-like collagen from the invertebrate *Stomolophus meleagris* and methods for its extraction. The subject invention also provides novel methods and compositions for the treatment of arthritis, in particular rheumatoid arthritis, by administering a therapeutically effective amount of pharmaceutical collagen-containing compositions of the invention so as to induce immune tolerance. The methods of the invention include the oral administration of the collagen containing compositions of the invention. Also included is formulated as a nutritional supplement, for instance, type II-like collagen formulated with a liquid or food substance.

Wistar Furth rats were divided into six groups and treated as follows. Groups One-Five were immunized with 400 μg of Bovine type II collagen (BII) in Complete Freund's Adjuvant (CFA). Group Six (negative control) was immunized with CFA without BII collagen.

Group One had been orally administered jellyfish collagen (JF) in mild acetic acid prior to immunization with BII collagen (pre-JF). Group Two was orally administered jellyfish collagen (JF) in mild acetic acid after immunization with BII collagen (post-JF). Group Three was orally administered BII collagen in mild acetic acid prior to immunization with BII collagen (pre-BII). Group Four was orally administered BII collagen in mild acetic acid after immunization with BB collagen (post-BII).

Group Five (positive control) and Group Six (negative control) were orally administered mild acetic acid without collagen. Groups One-Five received a booster injection of 200 μg of BII collagen in Incomplete Freund's Adjuvant 20 days post-immunization. The animals were evaluated and assigned an arthritic score as described in Example 3, below.

Figure 3:
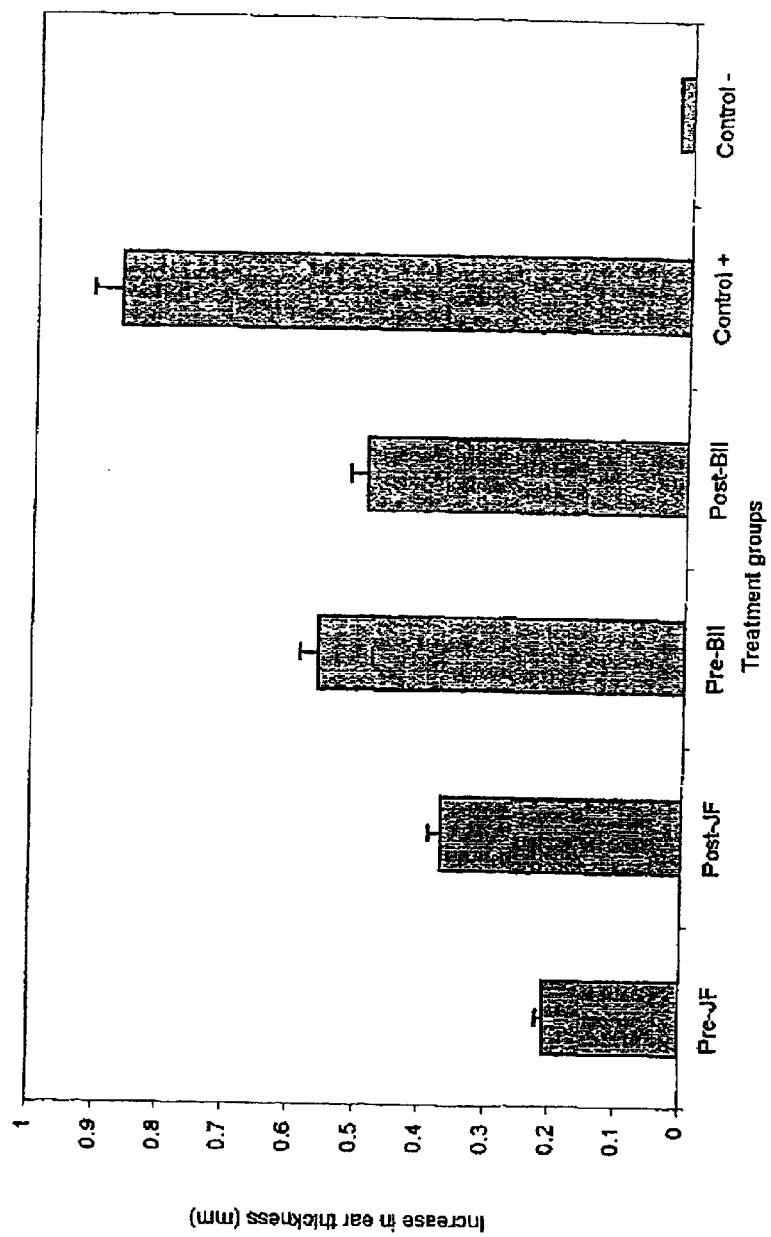

FIG. 3. Comparison of Delayed Type Hypersensitivity (DTH) Caused by Oral Administration of Jellyfish Collagen and Bovine Collagen in the Wistar Furth Rat Collagen-induced Arthritis Rheumatoid Arthritis Model.

Figure 2:
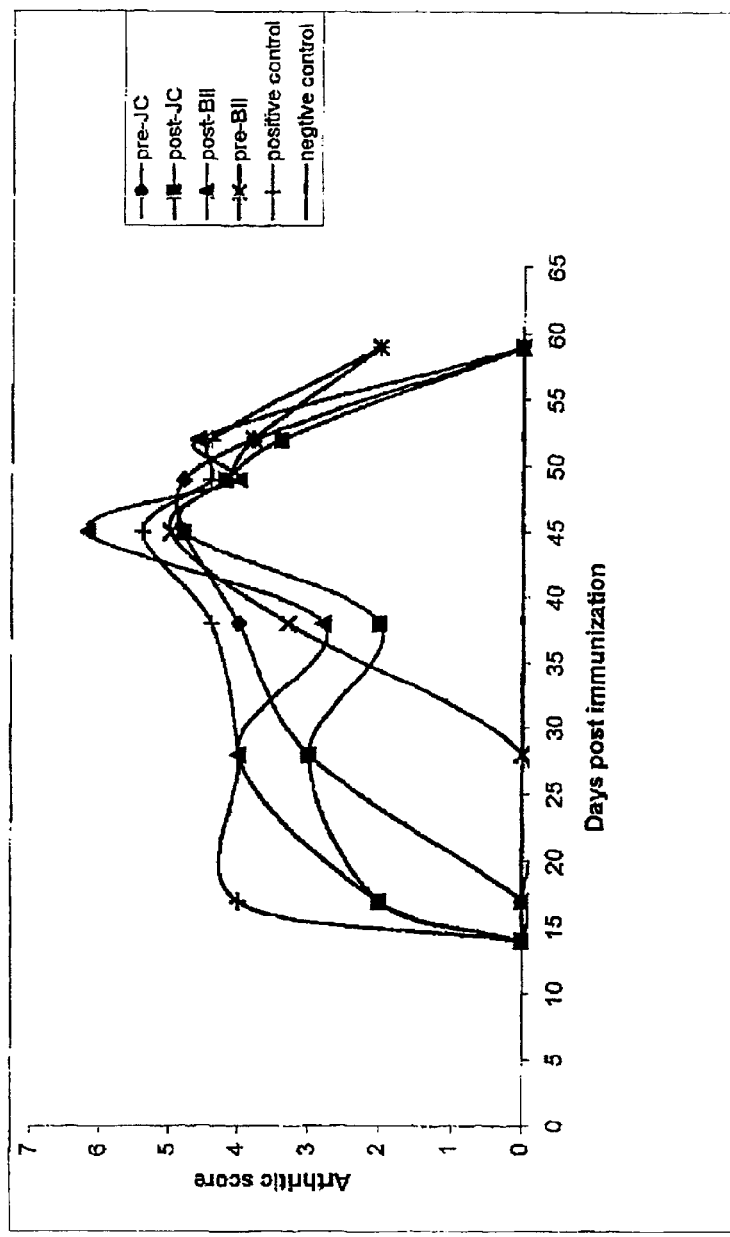
FIG. 2. Comparison Study of Suppression of Arthritis in Collagen-induced Arthritis Model by Oral Administration of Jellyfish Collagen vs. Oral Administration of Bovine Type II Collagen.

DTH was assayed in the Wistar Furth rats described in FIG. 2, above. Thirty days post immunization, all animals were injected with 50 μg of Bovine type II collagen (BII) on the right ear and ear thickness was assayed 72 hours post injection.

Figure 4:
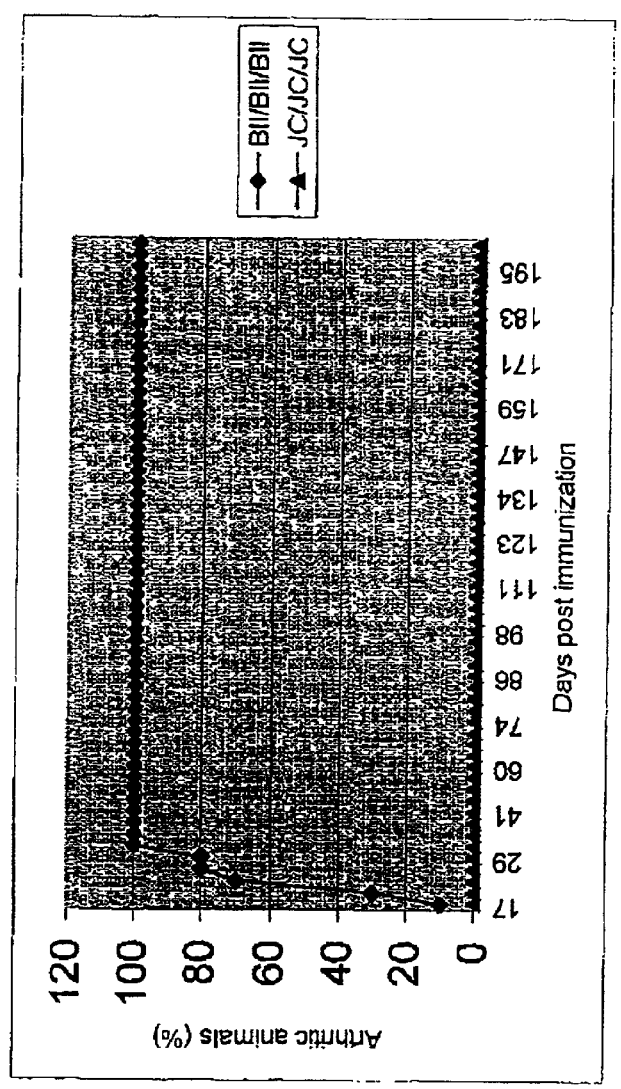

FIG. 4. Mean arthritis onset of Wistar Furth Rats immunized with bovine type II collagen or type II-like jellyfish collagen. Wistar Furth rats were immunized with either 400 μg of BII collagen with CFA (group BII/BII/BII) or type II-like collagen from jellyfish with CFA (group JC/JC/JC). On day 20 and 81 post-immunization, group BII/BII/BII rats were boosted with 200 μg of BII in Incomplete Freund's Adjvant; group JC/JC/JC rats were boosted with 200 μg of type II-like collagen in Incomplete Freund's Adjvant.

Figure 5:
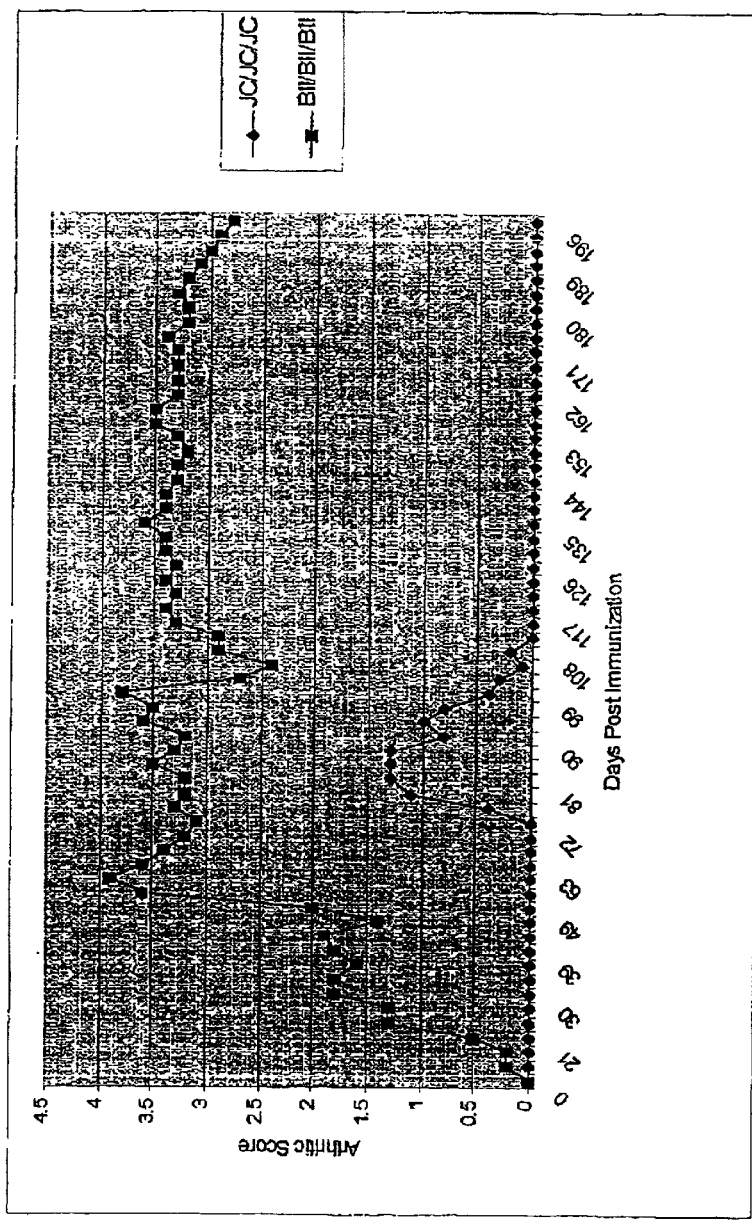

FIG. 5. Mean arthritis score of Wistar Furth Rats immunized with bovine type II collagen or type II-like jellyfish collagen, as described in FIG. 4, above.

DETAILED DESCRIPTION OF THE INVENTION

The present invention is concerned with the preparation of type II-like collagen from invertebrates. In particular, type H-like collagen from jellyfish of the class Scyphozoa, phylum Coelenterata, including the jellyfish *Stomolophus meleagris* is provided. The type II-like collagen is provided in substantially purified compositions for formulation into pharmaceutically acceptable compositions. Such type II-like compositions are useful for the treatment of autoimmune disorders.

By "type II-like collagen" is intended collagen with characteristics similar to those of type II collagen of mammals, such as the molecular mobility, salting-out concentration, high content of hydroxylysine, solubility properties, absence of disulfide bonds, and highly hygroscopic nature of the protein.

By "substantially homogeneous" type II-like collagen is intended type II-like collagen molecules in the substantial absence of other biological macromolecules, e.g., other contaminating types of collagen, polynucleotides, proteins, etc. Preferably a substantially homogeneous jellyfish collagen is at least 85% by weight (wt %), more preferably at least 90% by weight, most preferably at least 95%, 96%, 97%, 98%, 99% or greater by weight of the indicated biological macromolecules present. However, the term "biological macromolecules" does not include water, buffers, and other small molecules, especially molecules having a molecular weight of less than 1000 daltons. In no case does a substantially homogeneous type II-like jellyfish collagen encompass the collagen present in its natural source.

A substantially homogeneous jellyfish collagen is substantially free of natural contaminants. By collagen that is "substantially free of natural contaminants" is intended collagen that has, at some point, been purified to be substantially homogeneous. However, collagen that is substantially free of natural contaminants may be associated with other compounds. In no case does collagen substantially free of natural contaminants encompass the collagen present in its natural source.

Methods for the extraction of collagen from jellyfish are known in the art. See, e.g., Kimura et al.; Nagia et al. (1999); Nagai et al. (2000); and U.S. Pat. No. 5,925,736, which are incorporated herein by reference. Generally, jellyfish are subjected to mechanical disruption followed by solubilization of the disrupted tissue to create a solubilized collagen solution. The collagen is then precipitated and collected. Typically, solubilization is accomplished under mildly acidic conditions. Because all major collagen types (I-V) can be precipitated at roughly molar salt concentrations at acidic pH, precipitation is accomplished by the addition of salt to about 1.0 M, which results in a mixture of collagen types.

At neutral pH, however, type II collagen can be precipitated at the range of 3.5–4.5 M NaCl. Types I, III, and IV collagen are precipitated at 2.6 M, 1.5–1.7 M, and 1.7–2.0 M NaCl, respectively. Bornstein (1980) *Ann. Rev. Biochem.* 49:957–1003. Type V collagen from humans is precipitated at 4.5 M NaCl at neutral pH. Niyibizi et al. (1984) *J. Biol. Chem.* 259:14170–14174.

Figure 1:
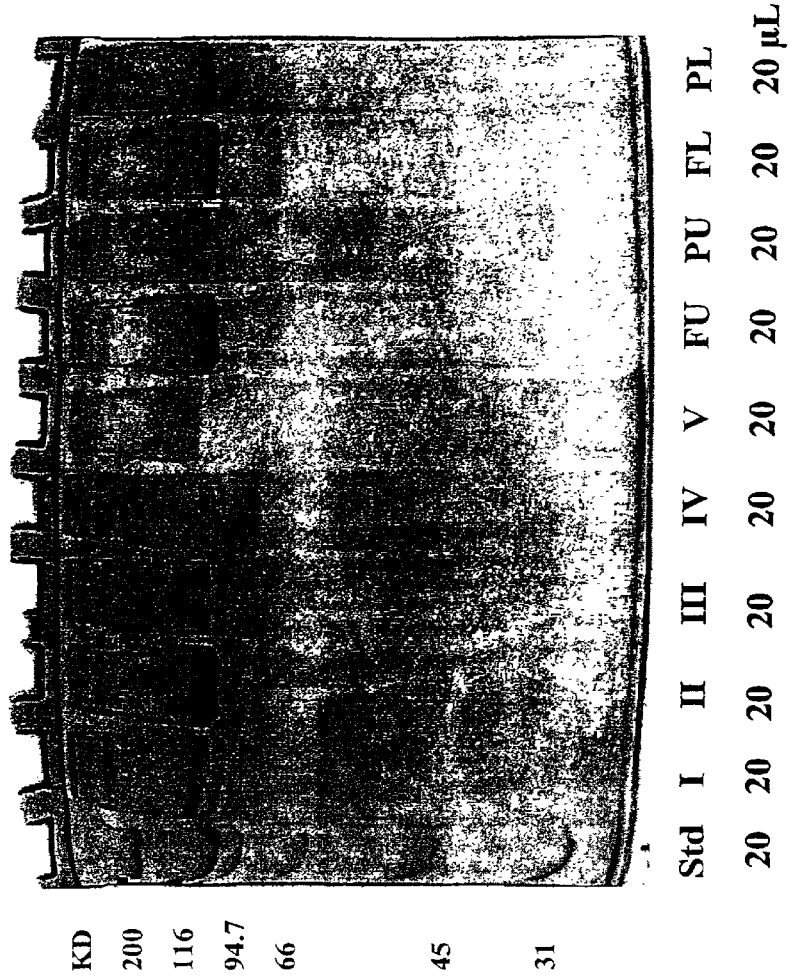
FIG. 1. SDS-PAGE of Jellyfish Collagen. Collagen from the following sources was obtained and subject to SDS-PAGE under non-reducing conditions. Samples are as follows (left to right): Standard (Lane 1), Vertebrate Type I Collagen Standard (Lane 2), Vertebrate Type II Collagen Standard (Lane 3), Vertebrate Type III Collagen Standard (Lane 4), Vertebrate Type IV Collagen Standard (Lane 5), Vertebrate Type V Collagen Standard (Lane 6), Fresh Cannonball Jellyfish Umbrella (Lane 7), Processed Cannonball Jellyfish Umbrella (Lane 8), Fresh Cannonball Jellyfish Legs (Lane 9), and Processed Cannonball Jellyfish Legs (Lane 10). SDS-PAGE gels (4% stacking/8% running) were prepared according to a standard protocol. See, e.g., Ausubel et al., *Current Protocols in Molecular Biology*, John Wiley & Sons (1998).

The major collagen of component of *Stomolophus meleagris* can be precipitated at 3.5 M NaCl in neutral pH. Based on the molecular mobility (see FIG. 1), salting-out concentration, high content of hydroxylysine, solubility properties, absence of disulfide bonds, and highly hygroscopic nature of the protein, the 3.5 M NaCl fraction was characterized as type II-like collagen, from which other collagen types had been excluded.

The exclusion of other collagen types in the 3.5 molar fraction at neutral pH was confirmed by SDS-PAGE. A sample of the neutral 3.5 M NaCl fraction and a sample of the acidic precipitation at 1.0 M NaCl, pH 2.5 were electrophoresed by SDS-PAGE and stained using standard methods. The 3.5 M NaCl fraction produces a single band. In contrast, the acidic precipitation at 1.0 M NaCl, pH 2.5, above, produces two to three bands with one dominating band (data not shown).

However, although type II-like collagen is similar to type II vertebrate collagen, there are differences. For instance, Cyanogen Bromide (CNBr) peptide mapping of type Ifl-ike collagen produces two major peaks. See Example 1, below. Further, comparison of the amino acid composition of vertebrate type II collagen and type II-like jellyfish collagen show that vertebrate type II collagen has a comparatively higher proline and hydroxyproline content, while type II-like collagen has a comparatively higher hydroxylysine and lysine content. Methods for determining amino acid content are known in the art. See, e.g., Kimura et al. (1983) and Miura et al. (1985), each of which is incorporated herein by reference.

In the present invention, jellyfish are separated and/or subjected to mechanical disruption followed by solubilization of the disrupted tissue. For instance, the whole jellyfish can be cleaned of mucus membranes and gonadal material, ground, and, optionally, lyophilized for future use. The tissue is then solubilized prior to collagen extraction. Alternatively, a part or parts of the jellyfish can be selected, such as umbrella, oral arms (also called legs), or both. The resulting solubilized collagen solution may be further treated, for instance to remove acid or base soluble contaminants, etc. See Example 1, below. The solubilized collagen solution is then adjusted to neutral pH. Collagens are then salt fractionated at neutral pH by increasing the salt concentration in defined increments. The precipitated collagen fraction produced at each increment is collected and separated from the supernatant. Crude type II-like jellyfish collagen is precipitated in the range of 3.0–3.5 M salt. Collagen yields using neutral precipitation were found to be nearly double that produced by acid precipitation.

In a preferred embodiment, fresh cannonball jellyfish are cleaned of mucus membranes and gonadal material, ground, and the tissue lyophilized. The lyophilized tissue is suspended in deionized water (1:1000 w/v), stirred for one hour, and centrifuged at 10,000 times gravity for 30 minutes. The residue is extracted with 1000 volumes (w/v) of 0.1N NaOH and stirred overnight at 4° C., then centrifuged at 10,000 times gravity for one hour. This step is repeated 3 times. The final precipitate is then washed thoroughly with distilled water.

Ten volumes (v/v) of 0.5 M acetic acid are added and the suspension is stirred for 2 days, then centrifuged at 10,000 times gravity for 30 minutes. This acid-extraction is repeated once and the final precipitate is washed with deionized water. The residue is digested with 10% pepsin (Sigma) in 0.5 M acetic acid for 48 hours at 4° C. and centrifuged at 10,000 times gravity for one hour. The supernatant is removed and extracted against 0.02 M $Na_2HPO_4$ for 3 days. The entire volume is centrifuged at 10,000 times gravity for one hour.

The resulting precipitate is washed with deionized water and dissolved in Tris-HCl buffer containing 1 M NaCl, pH 7.5. Collagen fractions are salted out by sequential addition of NaCl to a concentration of 1.8 M NaCl, 2.5 M NaCl, 3.0 M NaCl, 3.5 M NaCl, 4.0 M NaCl, and 4.5 M NaCl. After each addition of NaCl, the suspension is allowed to set for 24 hours at 4° C., followed by centrifugation to separate the residue from supernatant. At 1.8 M NaCl and 2.5 M NaCl concentrations, only trace amounts of precipitates are formed and obtained by centrifugation. At 3.0 M NaCl to 3.5 M NaCl concentration, substantial amounts of collagen is salted out and separated by centrifugation. Each fraction is washed with deionized water, then lyophilized. The 3.5 M fraction, i.e., containing substantially homogeneous type II-like collagen, is collected for use as a tolerizing antigen.

In general, the resulting collagen preparations are useful in a variety of medical or nutritional applications. In one embodiment, the type II-like collagen of the present invention is useful for the treatment of autoimmune disorders, including autoimmune arthritis, such as rheumatoid arthritis or juvenile arthritis, polychondritis, multiple sclerosis, rheumatoid arthritis, uveitis, allergies, and myasthenia. Thus, the invention provides a method for the treatment of arthritis, including rheumatoid arthritis, in a mammalian subject.

While extraction methods for the type II-like collagen from cannonball jellyfish, i.e., *Stomolophus meleagris*, is described, it is recognized that similar methods can be used to extract collagen from other species of jellyfish, such as *Ropelema nomadica* (data not shown). Type II-like collagen from other sources can be identified based on the molecular mobility, salting-out concentration, high content of hydroxylysine, solubility properties, absence of disulfide bonds, and highly hygroscopic nature of the protein.

Collagen from other jellyfish species suitable for use in the methods and compositions of the invention for the treatment of arthritis may be determined in vivo, using the protocols described herein to determine whether the collagen can induce immune tolerance. See Thompson et al. (1985) *Clinical and Experimental Immunology* 64:581–586, herein incorporated by reference. Alternatively, collagen can be tested in vitro with T cells from rheumatoid arthritis patients to determine if a given collagen derivative can stimulate suppressor T cells, induce clonal anergy, or induce other forms of immune tolerance. See Paul, ed., (1994) *Fundamental Immunology*, 2nd Ed., (Raven Press, New York), herein incorporated by reference.

By "treatment" or "treating" is intended both prophylaxis and amelioration of symptoms already present in an individual. Treatment comprises administering a therapeutically effective amount of type II-like collagen compositions disclosed herein to a subject in need thereof.

By "subject" is intended mammals, e.g., humans, dogs, cattle, horses, and the like. Preferably the subject undergoing treatment with the collagen compositions of the invention is human.

By "therapeutically effective amount" is intended a non-toxic dosage level sufficient to induce a desired biological result. It will be appreciated by the person of ordinary skill in the art that a therapeutically effective amount need not be completely effective in preventing the onset of a disease or in reducing the symptoms associated with the disease. Reduction of the severity of symptoms, delay in the onset of symptoms, or delay in the progression of severity of symptoms is desirable. Amounts for administration may vary based upon the diseased state of the mammal being treated, the dosage form, method of administration, patient factors such as age, sex, and severity of disease, or risk of developing arthritis, family history, genetic markers, early symptoms, and the like. Amounts that will constitute a therapeutically effective amount may also be based upon the factors stemming from the formulation of the collagen, i.e., inert components in the formulation, adjuvants, and the like. It is recognized that a therapeutically effective amount is provided in a broad range of concentrations. Such range can be determined based on in vivo assays or by monitoring and clinical assessment.

The present invention recognizes that type II-like collagen can induce oral tolerance, i.e., act as a tolerizing antigen. While the invention is not bound by any mechanism, it is believed that two mechanisms exist that primarily mediate oral tolerance. The first, active cellular suppression, involves regulatory T cell suppression of the activation and proliferation of lymphocytes specific for the tolerized antigen. The second, clonal anergy, renders T lymphocytes having a suitable receptor unresponsive. Small amounts of the tolerizing antigen are believed to favor active suppression, whereas large amounts of the tolerizing antigen favor clonal anergy. See Weiner et al. (1994) *Ann. Rev.* 1 mm. 12:809–835.

A possible range for the amount of collagen(s) and/or collagen(s) derivatives which may be administered per day may be in the range of from about 0.001 mg to about 200 mg. The effective amount can be determined by routine experimentation. For purposes of the present invention, generally a therapeutic amount will be in the range of about 1 µg/kg to about 1 mg/kg, more preferably about 5 µg/kg to about 0.8 mg/kg, and most preferably about 10 µg/kg to about 0.5 mg/kg, in at least one dose. Preferably, the amount administered is low, to favor the induction of immune tolerance by suppression instead of by clonal anergy. The pharmaceutical compositions containing the collagen may be formulated so as to provide a therapeutically effective amount in a single administration or in multiple administrations. Such regimens will vary depending on the severity of the disease and the desired outcome.

For example, the type II-like collagen of the invention can be administered for as short a period of time as several days. Alternatively, type II-like collagen can be administered once daily for two, three, or four days, up to, and including a period of one month, two months, or more. It is not necessary that the dose administered in each cycle be equivalent. The type II-like collagen can be administered as a single agent, in conjunction with agents that are standard of care for the particular condition involved, in conjunction with an antigenic booster, or as a combination of all three.

The treatment methods of the invention comprise the step of administering an effective amount of a composition of the invention, e.g., jellyfish type II-like collagen. The compositions administered in the subject methods are administered such that the collagen contacts the lymphoid tissue of the gut (Peyer's patches, etc.) so that immune tolerance is induced. The collagen may be administered with additional pharmaceutical compounds for the treatment of arthritis, such as anti-inflammatory agents, etc.

The subject compositions may be adapted for various types of administration, e.g., topically, orally, intranasally, by injection or by inhalation. Administration of collagen may be effected by many possible methods through the use of formulations comprising the subjected compositions that are designed for oral administration, i.e., the active components are not destroyed or inactivated in the mouth, stomach, or other portions of the digestive system prior to contacting the appropriate gut lymphoid tissue.

Compositions of the invention may optionally be formulated in association with a pharmaceutically acceptable carrier. Alternatively, compositions of the invention may optionally be formulated as a pharmaceutically acceptable salt thereof, in association with a pharmaceutically acceptable carrier.

A "pharmaceutically acceptable carrier" includes solids, semi-solids or liquid diluents, or an ingestible capsule, such as tablets, gelatin capsules, drops such as nasal drops, preparations for topical application such as ointments, jellies, creams and suspensions, aerosols for inhalation, nasal spray, liposomes, etc. In most cases, the collagen will comprise between 0.05 and 99%, or between 0.1 and 99% by weight of the preparation, for example between 0.5 and 20% for preparations intended for injection and between 0.1 and 50% for preparations intended for oral administration.

For oral administration, the agent can be contained in enteric forms to survive the stomach or further coated or mixed to be released in a particular region of the GI tract by known methods. For instance, the agent can be provided with a layer of gastric juice-resistant enteric film or coating having such properties that it is not dissolved at the acidic pH in the gastric juice, thereby preventing release of the collagen until the preparation reaches the intestines. Such coatings include cellulose acetate phthalate, hydroxypropyl-methylcellulose phthalates, etc. For the purpose of oral therapeutic administration, the collagen can be incorporated with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth, or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Oral compositions can also be prepared using a fluid carrier for use as a mouthwash, wherein the compound in the fluid carrier is applied orally and swished and expectorated or swallowed. Liquid preparations for oral application may be in the form of elixirs, syrups or suspensions. Such solutions typically contain from about 0.1% to 20% by weight of active substance, sugar and a mixture of ethanol, water glycerol, propylene glycol and optionally aroma, saccharine and/or carboxymethylcellulose as a dispersing agent. The type II-like collagen may also be formulated as a solid or liquid dietary supplement, i.e., incorporated with juice, etc.

The compositions of the invention may also be prepared as a sustained release formulation. One example of a sustained release formulation is a tablet, composed of several layers of the active ingredient that are separated by coatings that dissolve slowly. Alternatively the active ingredient may be divided into particles with coatings of different thickness compressed together with a carrier substance. Alternatively, the active ingredient may be incorporated into a fat and wax substances.

Administration can also be by transmucosal or transdermal means. Examples of pharmaceutical preparation for this route of administration include ointments, jellies, creams and suspensions, aerosols for inhalation, nasal spray, liposomes, etc. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

EXPERIMENTAL

Materials and Methods

Fresh cannonball jellyfish are obtained from the Gulf of Mexico. For instance, cannonball jellyfish have been harvested from the west coast of Florida. Other standard reagents and chemicals are obtained from commercial providers. Sources for such materials are known to the skilled artisan.

EXAMPLE 1

Extraction and Characterization of Type II-Like Collagen From *Stomolophus melagris*.

Fresh cannonball jellyfish are cleaned of mucus membranes and gonadal material, then ground. The tissue is then lyophilized to remove moisture, reduce bulk, and facilitate storage and handling for subsequent collagen extraction.

The lyophilized tissue is suspended in deionized water (1:1000 w/v), stirred for one hour. The suspension is then centrifuged at 10,000 times gravity for 30 minutes. This procedure removes water soluble substances, such as salt and water soluble proteins, including many enzymes.

The water insoluble residue is then extracted with 1000 volumes (w/v) of 0.1N NaOH. The suspension is stirred overnight at 4° C., then centrifuged at 10,000 times gravity for 1 hour. The alkali extraction is repeated 3 times. The final precipitate is then washed thoroughly with distilled water. This procedure removes alkali-soluble non-collagenous matter.

Ten volumes (v/v) of 0.5 M acetic acid is then added to the alkali-insoluble residue. The suspension is stirred for 2 days, then centrifuged at 10,000 times gravity for 30 minutes. This acid-extraction is repeated once and the final precipitate is washed with deionized water. This procedure removes acid-soluble proteins.

The acid insoluble residue is the digested with 10% pepsin in 0.5 M acetic acid for 48 hours at 4° C. The mixture is then centrifuged at 10,000 times gravity for one hour. The supernatant is removed and extracted against 0.02 M $Na_2HPO_4$ for 3 days to inactivate pepsin and precipitate collagen. The entire volume is centrifuged at 10,000 times gravity for 1 hour.

The resulting precipitate is washed with deionized water and dissolved in Tris-HCl buffer containing 1 M NaCl, pH 7.5. Collagen fractions are salted out by sequential addition of NaCl to a concentration of 1.8 M NaCl, 2.5 M NaCl, 3.0 M NaCl, 3.5 M NaCl, 4.0 M NaCl, and 4.5 M NaCl. After each addition of NaCl, the suspension is allowed to set for 24 hours at 4° C., followed by centrifugation to separate the residue from supernatant. At 1.8 M NaCl and 2.5 M NaCl concentrations, only trace amounts of precipitates are formed and obtained by centrifugation. At 3.0 M NaCl to 3.5 M NaCl concentration, substantial amounts of collagen is salted out and separated by centrifugation. Each fraction is washed with deionized water, then lyophilized. Substantially homogeneous type II-like collagen is found in the 3.5 M fraction.

CM-52 Chromatography. After extraction, ten milligrams of type II-like jellyfish collagen was dissolved in 5 mL of 20 mM sodium acetate buffer (pH 4.6) containing 6 M urea. The sample was denatured at 45° C. for 30 minutes. The denatured type II-like collagen was then applied to a CM-52 column (1.5×7 cm) equilibrated with buffer (Bio-Rad Econo Chromatography System®). Separation was achieved using a linear salt gradient (O to 0.2 M NaCl) over a total volume of 160 mL in the same buffer. Fractionation was monitored at 280 nm and individual fractions were analyzed by SDS-PAGE. Two major peaks (peaks 1 and 3) and one minor peak (peak 2) were observed during elution (data not shown).

Cyanogen Bromide (CNBr) peptide mapping protocol. Two milligram samples taken from each of the three eluted peaks, above, were subjected to CNBr (1981) *J. Biol. Chem.* 256:13230–13234, which is incorporated herein by reference. The resulting material was subject to SDS-PAGE on a 10% SDS-PAGE gel. Banding patterns for the major peaks 1 and 3 were identical. The banding pattern for the minor peak 2 differed from the major peaks.

EXAMPLE 2

Comparison of Type II-Like Jellyfish Collagen to Major Vertebrate Collagen Types by SDS-PAGE.

Samples of the major vertebrate collagen types (I–V) were obtained from a commercial source. Cannonball jellyfish type II-like collagen was prepared as described above. All samples were subject to SDS-PAGE under non-reducing conditions.

The gel was loaded as follows (left to right): Molecular Weight Standard (5 μg) (Lane 1), Vertebrate Type I Collagen Standard (Lane 2), Vertebrate Type II Collagen Standard (Lane 3), Vertebrate Type III Collagen Standard (Lane 4), Vertebrate Type IV Collagen Standard (Lane 5), Vertebrate Type V Collagen Standard (Lane 6), Fresh Cannonball Jellyfish Umbrella (Lane 7), Processed Cannonball Jellyfish Umbrella (Lane 8), Fresh Cannonball Jellyfish Legs (Lane 9), and Processed Cannonball Jellyfish Legs (Lane 10).

All samples contained 15 µg of collagen. SDS-PAGE gels (4% stacking/8% running) were prepared according to a standard protocol. See, e.g., Ausubel et al., Current Protocols in Molecular Biology, John Wiley & Sons (1998). The banding pattern and mobility of type II-like jellyfish collagen is most similar to that of vertebrate type II collagen. See FIG. 1.

EXAMPLE 3

Comparison Study of Suppression of Arthritis in Collagen-induced Arthritis Model by Oral Administration of Jellyfish Collagen vs. Oral Administration of Bovine Type II Collagen.

Collagen-induced arthritis (CIA) shares clinical, histological, immunological, and genetic features with human RA and has been used as an animal model in the study of RA for over twenty years. Terato et al. (1985) *J. Exp. Med.* 162:637–46. This model was used to study the effects of oral feeding of jellyfish type II-like collagen. The induction of CIA was done according to the methods of Yoshino (1998) *J. Immunol* 160:3067–71, which is incorporated herein by reference.

Eight-week old Wistar Furth rats were obtained from Harlan Sprague Dawley, Inc. (Walkersville, Md.). Type II-like collagen was obtained from *Stomolophus melagris* as described above.

Wistar Furth rats were divided into six groups and treated as follows. Groups One-Five were immunized with 400 µg of Bovine type II collagen (BII) in Complete Freund's Adjuvant (CFA). Group Six (negative control) was immunized with CFA without BII collagen.

Group One had been orally administered 10 µg doses of jellyfish collagen (JF) in 0.5 mL acetic acid (0.005 N) prior to immunization with BII collagen (pre-JF). Group Two was orally administered 10 µg doses of jellyfish collagen (JF) in 0.5 mL acetic acid (0.005 N) after immunization with BII collagen (post-JF). Group Three was orally administered 5 µg doses of BII collagen in 0.5 mL acetic acid (0.005 N) prior to immunization with BII collagen (pre-BII). Group Four was orally administered 5 µg doses of BII collagen in 0.5 mL acetic acid (0.005 N) after immunization with BII collagen (post-BII).

Group Five (positive control) and Group Six (negative control) were orally administered 0.5 mL acetic acid without collagen. Groups One-Five received a booster injection of 200 µg of BII collagen in Incomplete Freund's Adjuvant 20 days post-immunization. Regimen and results are summarized in Table 1, below.

TABLE 1

JC: Jellyfish collagen; BII: Bovine type II collagen.

| Group | Oral Treatment | Onset Day | % Incidence |
|---|---|---|---|
| Pre-JC (Group One) | 10 µg JC per day for 6 days prior to immunization. | 28.8 ± 2.3 | 100% |
| Post-JC (Group Two) | 10 µg JC per day for 6 days after immunization. | 26.8 ± 1.1 | 100% |
| Pre-BII (Group One) | 5 µg BII per day for 6 days prior to immunization. | 31.4 ± 1.4 | 100% |
| Post-BII (Group Two) | 5 µg JC per day for 6 days after immunization. | 23.4 ± 1.8 | 100% |
| Positive Control (Group Five) | 0.5 mL of 0.005M acetic acid for 6 days before and for 6 days after immunization. | 19.0 ± 5.7 | 100% |
| Negative Control (Group Six) | 0.5 mL of 0.005M acetic acid for 6 days before and for 6 days after immunization. | 0.0 ± 0.0 | 0% |

The animals were then periodically monitored for 65 days after immunization. The animals were evaluated and assigned an arthritic score as follows. Each paw was subjectively graded on a scale of 0–4 based on the degree of inflammation and swelling of feet, digits, and ankles. Severe inflammation would be scored as 1, whereas severe inflammation coupled with severe swelling of feet, digits, and ankles, combined with loss of mobility, would be scored as a 4 for each individual limb. Thus, the maximum possible arthritic score per animal was 16 (4 per limb).

Groups pre- and post-fed jellyfish collagen (Pre-JF and Post-JF), i.e., Groups One and Two, respectively, showed significantly reduced incidence, onset, and severity of arthritis. See FIG. 2. The pre-fed group (Pre-BII), i.e., Group Three, showed reduced incidence, onset, and severity of arthritis. However, the post-fed group (Post-BII) did not exhibit the same suppression.

EXAMPLE 4

Comparison of Delayed Type Hypersensitivity (DTH) Caused by Oral Administration of Jellyfish Collagen and Bovine Collagen in the Wistar Furth Rat Collagen-Induced Arthritis Rheumatoid Arthritis Model DTH was assayed in the Wistar Furth Rat Collagen-Induced Arthritis Rheumatoid Arthritis Model. Thirty days post immunization, rats from Example 3, above, were injected with 50 µg of Bovine type II collagen (BII) in 20 µL 0.1 N acetic acid on the right ear. As a negative control, the left ear was injected with 0.1 N acetic acid. Ear thickness was assayed before and 72 hours post injection. The increase in the left ear thickness was subtracted from the thickness of the right ear to give the value due to the specific response to the injected antigen. DTH in rats fed JF collagen, as measured by increased ear thickness, was demonstrably lower than in rats fed BII collagen. However, DTH was lower in both test groups, as compared to the positive control group. See FIG. 3.

EXAMPLE 5

Comparison of Delayed Type Hypersensitivity (DTH) Caused by Oral Administration of Substantially Homogeneous Jellyfish Collagen vs. Dry Jellyfish Tissue Powder in the Wistar Furth Rat Collagen-Induced Arthritis Rheumatoid Arthritis Model Eleven-week old Wistar Furth Rats were randomly divided into groups. CIA was induced as described in Example 3, above. Substantially homogeneous jellyfish collagen was obtained as described in Example 1, above. Dry jellyfish tissue containing roughly 50% jellyfish collagen was obtained by drying jellyfish tissue which had not been subject to the extraction protocol described, above. Either prior or subsequent to immunization with BII, test groups were then fed a predetermined amount of substantially homogeneous jellyfish collagen or dry jellyfish tissue. Positive and negative controls were as described in Example 3 and 4, above.

Thirty days post immunization, all rats were injected with 50 μg of Bovine type II collagen (BII) in 20 μL of 0.001 N acetic acid on the right ear. As a negative control, the left ear was injected with 0.001 N acetic acid. Ear thickness was assayed before and 72 hours post injection. The increase in the left ear thickness was subtracted from the thickness of the right ear to give the value due to the specific response to the injected antigen. At low oral doses of substantially homogeneous jellyfish collagen and dry jellyfish tissue (5 μg jellyfish collagen and 110 g of dry jellyfish tissue, respectively), DTH was significantly lower in rats fed with jellyfish collagen as compared to dry jellyfish tissue and the positive control (data not shown).

EXAMPLE 6

Mean Arthritis Score and Onset of Wistar Furth Rats Immunized With Bovine Type II Collagen or Type II-Like Jellyfish Collagen Wistar Furth rats were immunized with either 400 μg of BII collagen with CFA (group BII/BII/BII) or type II-like collagen from jellyfish with CFA (group JC/JC/JC). On day 20 and 81 post-immunization, group BII/BII/BII rats were boosted with 200 μg of BII in Incomplete Freund's Adjvant; group JC/JC/JC rats were boosted with 200/g of type II-like collagen in Incomplete Freund's Adjvant. All animals were monitored for 200 days, as described in Example 3, above. All BII immunized animals developed arthritis symptoms. See Figure Four. Type II-like collagen immunized animals did not develop vivid arthritis, although some brief inflammation was observed after the 81-day boost-injection. See Figure Five.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. Type II-like collagen isolated from one or more species of jellyfish, said collagen comprising at least 85 wt % of collagen-protein.

2. The type II-like collagen of claim 1, wherein said collagen comprises at least 90 wt % of collagen-protein.

3. The type II-like collagen of claim 1, wherein said collagen comprises at least 95 wt % of collagen-protein.

4. The type II-like collagen of claim 1, wherein said collagen comprises at least 99 wt % of collagen-protein.

5. The type II-like collagen of claim 1, wherein said species is *Stomolophus meleagris*.

6. The type II-like collagen of claim 5, wherein said jellyfish comprise one or more elements selected from the group consisting of the umbrella, arms, and the whole organism.

7. The type II-like collagen of claim 1, produced by the process comprising:
   a. extracting acid insoluble collagen from one or more jellyfish species to form a solubilized collagen solution;
   b. salt fractionating said collagen solution by precipitating a fraction of collagen from said solubilized collagen solution at a pH between 7.0 and 8.0 by sequentially increasing the molarity of salt to 1.8 M, 2.5 M, 3.0 M, 3.5 M, 4.0 M, and 4.5 M and removing said precipitated collagen fraction after each sequential increase; and
   c. collecting the collagen fraction precipitated in the range of 3.0–3.5 M salt.

8. The type II-like collagen of claim 7, wherein said salt comprises one or more alkali metal halides.

9. The type II-like collagen of claim 7, wherein said salt comprises NaCl.

10. The type II-like collagen of claim 7, wherein said salt fractionating is carried out at a pH of 7.5.

11. Type II-like collagen, produced by the process comprising:
   a. extracting acid insoluble collagen from *Stomolophus meleagris* to form a solubilized collagen solution;
   b. salt fractionating said collagen solution by precipitating a fraction of collagen from said solubilized collagen solution at pH 7.5 sequentially increasing the molarity of salt 1.8 M, 2.5 M, 3.0 M, 3.5 M, 4.0 M, and 4.5 M and removing said precipitated collagen fraction after each sequential increase; and
   c. collecting the collagen fraction precipitated in the range of 3.0–3.5 M salt.

12. A method of treating arthritis in a subject in need thereof, said method comprising administering a therapeutically effective amount of a type II-like collagen from one or more species of jellyfish to said subject, said collagen comprising at least 85% wt % of collagen-protein.

13. The method of claim 12, wherein the arthritis is rheumatoid arthritis.

14. A method for modulating an autoimmune response in a mammal comprising administering a therapeutically effective amount of a type II-like collagen from one or more species of jellyfish to said mammal, said collagen comprising at least 85% wt % of collagen-protein.

15. A pharmaceutical composition comprising a type II-like collagen from one or more species of jellyfish and a pharmaceutically acceptable carrier, said collagen comprising at least 85% wt % of collagen-protein.

* * * * *

UNITED STATES PATENT AND TRADEMARK OFFICE
CERTIFICATE OF CORRECTION

PATENT NO. : 6,894,029 B1
DATED : May 17, 2005
INVENTOR(S) : Hsieh

It is certified that error appears in the above-identified patent and that said Letters Patent is hereby corrected as shown below:

<u>Coulmn 14,</u>
Line 34, after "salt" insert the word -- to --.

Signed and Sealed this

Nineteenth Day of July, 2005

JON W. DUDAS
*Director of the United States Patent and Trademark Office*